United States Patent
Geutebrueck

(10) Patent No.: US 7,096,126 B2
(45) Date of Patent: Aug. 22, 2006

(54) METHOD AND DEVICE FOR DETECTING FUNCTIONAL AND METABOLIC DATA OF A LIVING ORGANISM

(75) Inventor: Ernst Geutebrueck, Brandenburg (DE)

(73) Assignee: Texmed Aktiengesellschaft, Brandenburg (DE)

( * ) Notice: Subject to any disclaimer, the term of this patent is extended or adjusted under 35 U.S.C. 154(b) by 236 days.

(21) Appl. No.: 10/474,398

(22) PCT Filed: Apr. 9, 2002

(86) PCT No.: PCT/DE02/01378

§ 371 (c)(1),
(2), (4) Date: Oct. 9, 2003

(87) PCT Pub. No.: WO02/082983

PCT Pub. Date: Oct. 24, 2002

(65) Prior Publication Data

US 2004/0133353 A1 Jul. 8, 2004

(30) Foreign Application Priority Data

Apr. 12, 2001 (DE) ................. 101 19 527

(51) Int. Cl.
*G06F 19/00* (2006.01)
(52) U.S. Cl. .......................... 702/32; 702/22
(58) Field of Classification Search ............. 702/22, 702/32; 600/554
See application file for complete search history.

(56) References Cited

U.S. PATENT DOCUMENTS

| | | | |
|---|---|---|---|
| 6,047,203 A | 4/2000 | Sackner et al. ............. 600/388 |
| 6,088,615 A | 7/2000 | Masuo ....................... 600/547 |
| 6,212,416 B1 * | 4/2001 | Ward et al. ................. 600/345 |
| 6,544,193 B1 * | 4/2003 | Abreu ........................ 600/558 |
| 6,565,509 B1 * | 5/2003 | Say et al. ................... 600/365 |

FOREIGN PATENT DOCUMENTS

| | | |
|---|---|---|
| DE | 32 28 551 | 2/1984 |
| DE | 195 18 511 | 11/1995 |
| DE | 195 19 051 | 11/1996 |
| DE | 196 39 224 | 3/1998 |
| DE | 196 39 228 | 3/1998 |
| EP | 1 091 215 | 4/2001 |
| FR | 2 750 029 | 12/1997 |
| WO | 95 20349 | 8/1995 |
| WO | 96 33651 | 10/1996 |
| WO | 98 28039 | 7/1998 |
| WO | 00 15110 | 3/2000 |

* cited by examiner

Primary Examiner—John Barlow
Assistant Examiner—Douglas N Washburn
(74) Attorney, Agent, or Firm—Jordan and Hamburg LLP

(57) ABSTRACT

The invention relates to a device and method for detecting functional data of a living organism and for controlling the corporeal values of the living organism in a pain-free and simple manner as often as required. The influences of existing natural and artificial electric, electrochemical and electromagnetic fields are determined. Electrodes are used alternately as sensors and as actuators, and the electrodes detect and transmit values to a downstream data detection unit.

38 Claims, 3 Drawing Sheets

Figure 1:
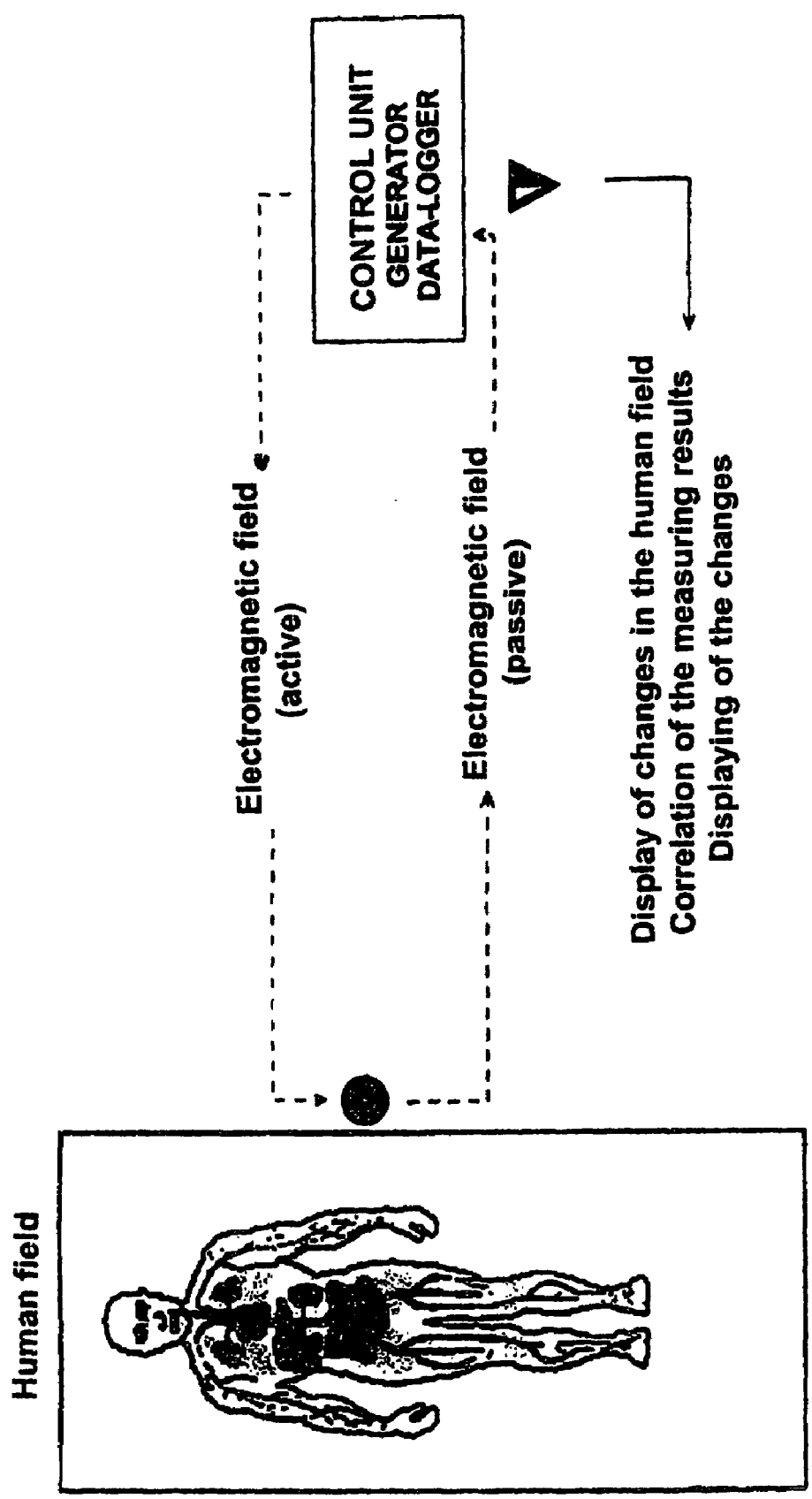

METHOD AND DEVICE FOR DETECTING FUNCTIONAL AND METABOLIC DATA OF A LIVING ORGANISM

The invention relates to a method for mobile or in-patient detecting corporeal functional and metabolic data of a living organism, and a device for carrying out said method.

Many facilities are known whose measuring techniques are based on taking blood sample from patients and indirect evaluating these samples. Use and evaluating are painful and complicated, and a special precision in this procedure is necessary. This is a problem in active life and for elder people. Therefore, tests often are carried out in too limited frequencies or wrongly so that often only incomplete results are available for the physician in charge.

Portable measuring instruments are known, too, in particular for example measuring instruments according to the patent specifications DE 196 39 224 and 196 39 228. In these patent specifications, the concentration of at least one substance is determined by means of measuring optics and a circuitry for evaluation. Moreover, according to the patent specification DE 32 28 551, a method for detecting the blood sugar level is known. In this method, blood sugar is determined in the presence of interfering substances by means of a measuring electrode with a before connected membrane. In this case, both components form an electrocatalytic blood sugar sensor. The measuring electrode is connected with a potentiostat, and a reaction potential and a measuring potential are detected. The electric current flowing during a measuring period is evaluated as a measuring signal. In the invention, a third potential, that is more negative than the measuring potential, is impressed to the measuring electrode after the reaction potential and before the measuring potential for a short time.

Moreover, a transcutaneous non-invasive method for determination of concentration of substances in blood according to the patent specification DE 195 18511 is known. In this invention, substances in the blood of a patient such as lactate, glucose, cholesterin, blood sugar, alcohol, drugs and other substances are determined in the following way:
a) A signal corresponding to the amount of a substance and to the amount of water in a given body is produced by spectroscopic methods and is measured.
b) The concentration in water is detected by the ratio of the signal value and the amount of a substance and of water.
c) From this ratio, the value of concentration of a substance in blood is calculated Moreover, a method and a device for polarometric determination of substances in the human body according to the patent specification DE 195 19 051 are known. In this invention, scattered light which escapes from a body region supplied with blood which is irradiated with linear-polarized light is analyzed. From the correlation between the detected rotational angle of polarization and the concentration of blood sugar, the particular blood sugar level is determined.

Generally, the majority of all known solutions suffers from disadvantages that it is necessary to take a blood sample from the patient and to evaluate this blood indirectly. In addition, the use of the customary invasive measuring methods requires an precise handling during an exactly defined period of time, and this is not satisfiable for certain disabled people. An additional serious disadvantage of all known and used devices consists in the insufficient data collection and (manual) filing by the patients. Apart from the fact that the data often is input insufficiently and the results are "massaged", the "paper" is unsuited for physicians as documentation for the detailed statistical interpretation because of the necessary time involved and missing software.

Object of the invention is to develop a method and a device which it makes possible for patients to carry out a self-checking of their corporeal values. This method on the living organism is painless, easy to use and practicable as often as required. Simultaneously, an individual data collection is possible.

The object is achieved by a method and a device for mobile or in-patient detecting corporeal functional and metabolic data of a living organism in a non-invasive way. For this, a substance which supports the influencing of existing natural and artificial electric, electrochemical, and electromagnetic fields is in the organism of a test person. According to this invention, it can be an lactate, an alcohol, cholesterin, stearin, protein, drugs, blood lipids, blood sugar, or glucose.

Electrodes are installed on the skin or nearly of the skin or are implanted in the body surface area of the test person. These electrodes are used alternately as sensor and as actuator, register caused and reflected signals and save these signals. The saved signals are input in a following computer system. Then sum values are calculated from the detected values on the basis of the course of time. These sum values are assigned to reference values and displayed regularly together with these reference values for comparison purposes. The data can be displayed on a screen but also on a writer. Both devices can be connected with a printer for data output of the detected values. The detected and balanced values can also be input in a data storage system for comparison, for further disposal and for recalling them if required.

The signal for assessment of the test person can be obtained continuously or discontinuously.

The available natural and artificial electric, electrochemical and electromagnetic values are physical parameters. A relevant physical parameter can be the field strength. It is also possible to register the density of field lines, a potential difference, an amperage, a voltage, or at least two quantities in combination. For storage and documentation purposes, the body temperature, the skin resistance, and the gas exchange through the skin per unit of time are relevant.

Referring to specific relevant body regions of the test person, it is possible to influence relevant skin areas as a whole or partially and concentrated. The data collection is possible point-like, in the form of a line, or in the form of an area. It is also possible to adapt the arrangement to the relevant skin areas, for example in the form of a matrix. It is also possible to implant at least one electrode in the body of the test person. An arrangement of the electrodes outside of the test person is disregarded here.

A device according to this invention, first, comprises of electrodes which can be used as sensors or as actuators. These electrodes are arranged with reference to the skin surface of the test person and are electrically/electronically connected with an analog changeover facility which is arranged before an operational amplifier stage. The operational amplifier stage consists of an impedance converter preamplifier with filter. An analog-digital converter with a digital signal processor is arranged after the operational amplifier stage which is for conditioning. This processor is connected to a computer stage which processes and stores the normalized and digitized measuring values. Therefore, the computer stage can preferably have an integrated storage module.

When the individual components of the device according to this invention are arranged separately, it can designed so that the data is transmitted wireless. But it is also possible to equip the individual components with an optical communication interface for transmitting the data.

The operational amplifier stage is adapted to the physical properties of the electrodes. A preferential version according to this invention intends to equip the analog-digital converter with the signal processor scalably according to the number of the used primary contacts. Preferably, the computer stage can be designed also scalably.

A further preferential version according to the invention intends that the computer stage controls the generator for adaptive stimulation and with this the changeover between sensor and actuator operation.

Preferably, a display is arranged after the computer stage in order to interpret the obtained diagrams.

To eliminate detected interferences, the operational amplifier stage is equipped with an adaptive filter element At least individual components can be implanted in the living organism. When the whole unit is sufficiently miniaturized it is also possible to arrange it in the living organism.

Starting point for the development of the method and for the use according to the invention was that there is a natural human field which can be established in the living organism. I was also established that the influence of substances in blood, which can be correlated, is measurable as abnormality in the natural human field. This makes it possible to use advantageously the method and the device according to the invention in a complete non-invasive way.

Therefore, it is possible to simplify considerably the continuous checking of corporeal values of a living organism by means of a non-invasive method. It is also possible to adjust continuously and stably corporeal values during a medical treatment.

It is also possible to obtain body values for the assessment of metabolic phenomena such as change of blood substances, blood alcohol, glucose, muscle efficiency, skin resistance, cutaneous circulation, pain location and other values of that kind from a seemingly healthy organism.

All data can be stored, analyzed and visualized separately for each person, can be displayed as individual daily profiles, weekly profiles and/or any other time profiles of physical data and their consequences such as concentration of substances and so on, and can be telecommunicated in other data systems.

It is a disadvantage of customary methods that they are complicated because of use of a lot of paper, when established data are collected, and mistakes, which are connected with that. This disadvantage is eliminated by the computer-aided data collection and the possibility, the established data to transfer to a specialist for further medical treatment or something like that.

In the following, the invention is described on the basis of an embodiment, in which the method as well as the device are explained in detail.

In the accompanying drawings show

Figure 2:
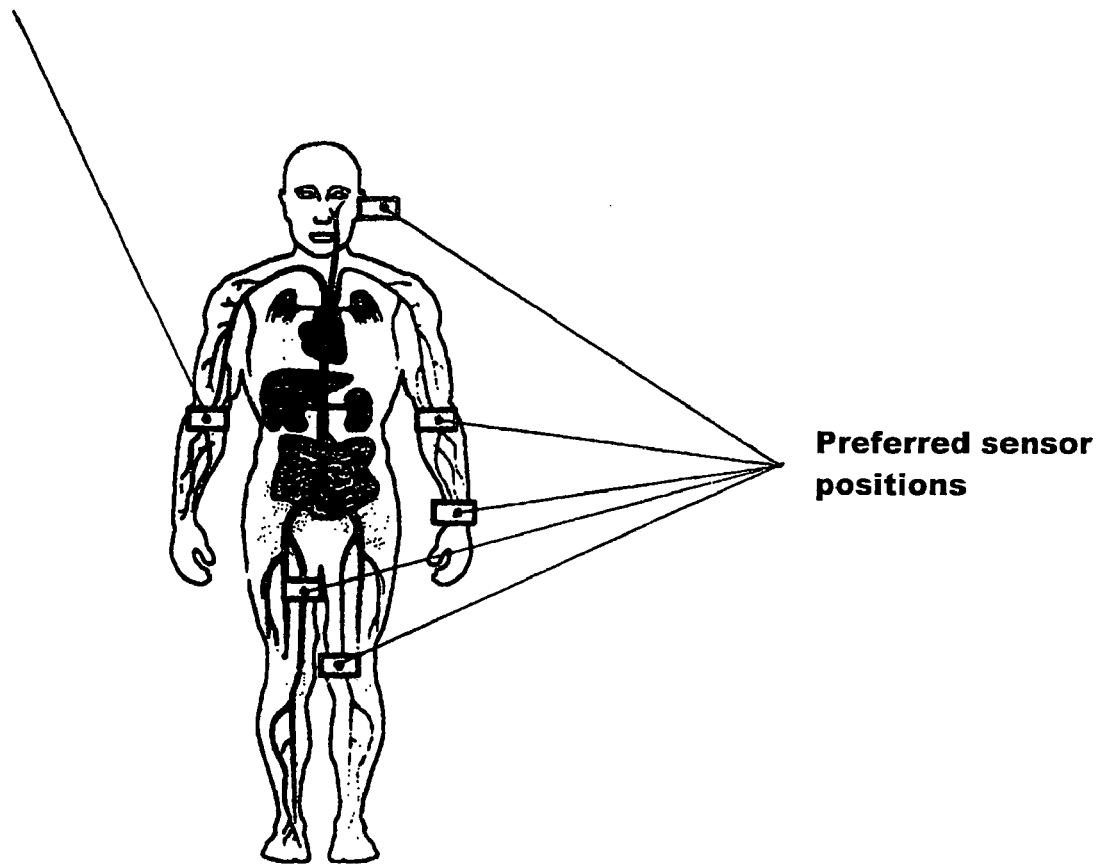
Figure 3:
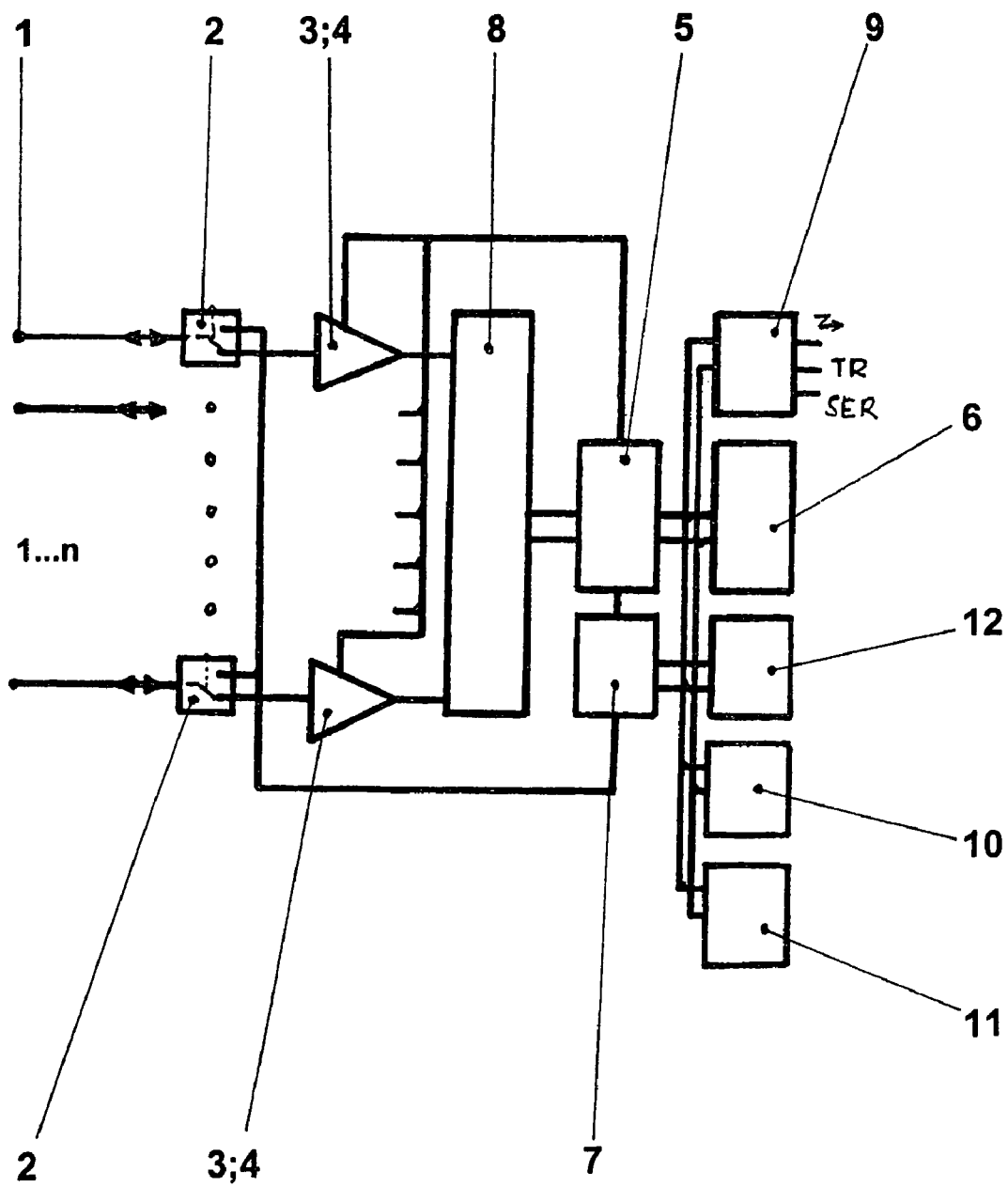

FIG. 1 the basic principle of course of measurement in case of use of the method according to the invention, FIG. 2 a presentation of preferred sensor positions on a human organism, and FIG. 3 a principle circuitry of a device equipped according to the invention.

A number of 1 . . . n electrodes 1 is fixed onto the body surface of a test person. All well-tolerated precious metals (gold, silver, platinum) or also conductive plastics or ceramics can be used as conductive material. All insulating substances such plastics or textiles can be used as carrier for the electrodes. In the embodiment, 6 electrodes are used which are miniaturized and embedded in conductive rubber. The rubber is enclosed for its fixture in a flexible polymer so that it adapts to the body of the test person.

The electronic system is also arranged on the carrier. The carrier is also intended to fix it on the body of the test person.

The electrodes 1 are designed so that they can act as sensor as well as actuator.

The component after the electrodes is the signal conditioning (A). In this component, an arrangement exists consisting of the single channel analog switch 2, the impedance converter preamplifier 3 and the filter 4. The latter form together the operational amplifier stage as unit.

If the electrodes 1 are used as sensor, the sensor signal is input in the impedance converter preamplifier 3. The after connected filter 4 achieves two objects. First, it is supposed to suppress interferences caused by induced fields in the environment and, second, it is supposed to limit the signal that is to transfer for data converting. In the embodiment, the filter 4 is designed multistage actively. The filter parameters are adapted and adjusted by means of the digital signal processor 5 and the processor 6. In this way, an analog signal is available that is suitable for processing.

If the electrodes are used as actuator, they are linked to the generator 7 by means of the single channel analog switch 2.

The data converting is carried out in the component C. In this component, a scalable interface is integrated in the data converting stage 8 which is linked to the signal processor 5 so that it is possible to operate several electrodes. Thus the electrodes 1 can be used as single elements or as matrix on the data converting stage 8. The selecting is achieved by the processor 6.

A high-resolution rapid analog-digital converter 8 is after connected to the scalable interface. This converter is provided with a signal processor interface. The analog-digital converter 8 is selected by the signal processor 5 and serves as data source for the signal processor 5. In the signal processor 5, the arriving data stream is preprocessed by detecting and eliminating the interferences. Moreover, the parameters for the adaptive filter are determined.

All raw data is transferred via a bus system, and the processor 6 controls the signal processor 5 via a control bus.

The generator 7 in this component is also controlled via this bus system (data bus and control bus). Several stored signal courses. Further parameters for the generator 7 are intensity and frequency. If new signal courses are synthesized, these can be stored specifically for each user.

The component D is the so-called controller segment. It serves as central control instance in the system. It observes all system functions, generates cyclically self-tests and carries out the online calibration of the whole system. It can also observe comparison measurements using classical analytical methods.

The components communication module 9, storage unit 12, system display 10, and keyboard 11 are connected with the controller via the bus system. The communication module 9 is designed in modular technique, and therefore it can be adapted to different transmission channels. It is also possible to implement software or hardware protocols.

The storage unit 12 is intended for long-term storage of the obtained data and for temporary intermediate storage of the current data. These storage unit 12 is preferably subdivided into a storage, which is implemented in the system as an integral part, and a extendable external storage.

A further external storage device can be equipped with interchangeable storage devices.

A specific evaluation program carries out the analysis of the measuring data for each person separately and program steps such as a correlation which, for example, reference data for these people, historical values and values like that, and deviations of time values and values like that. Moreover, the evaluation program carries out calculations such as calculations for determining the concentration of particular chemical substances.

Reference Signs
Electrodes 1
Single channel analog switch 2
Impedance converter preamplifier 3
Filter 4
Signal processor 5
Processor 6
Generator 7
Analog-digital converter 8
Communication module 9
System display 10
Keyboard 11
Storage unit 12

The invention claimed is:

1. A method for detecting corporeal functional and metabolic data of a person by detecting in the person a substance which influences at least one of natural and artificial electric, electrochemical, and electromagnetic fields in the person, comprising:
    applying electrodes to the person;
    activating the electrodes alternatingly as sensors and as actuators;
    detecting signals resulting from said activating of the electrodes;
    said signals representing changes of a physical parameter of said natural and artificial electric, electrochemical, and electromagnetic fields;
    registering and storing the detected signals;
    inputting the stored signals into data processing equipment;
    processing the stored signals in the data processing equipment thereby to measure said substance;
    wherein said physical parameter is strength of said field.

2. A method for detecting corporeal functional and metabolic data of a person by detecting in the person a substance which influences at least one of natural and artificial electric, electrochemical, and electromagnetic fields in the person, comprising:
    applying electrodes to the person;
    activating the electrodes alternatingly as sensors and as actuators;
    detecting signals resulting from said activating of the electrodes;
    said signals representing changes of a physical parameter of said natural and artificial electric, electrochemical, and electromagnetic fields;
    registering and storing the detected signals;
    inputting the stored signals into data processing equipment;
    processing the stored signals in the data processing equipment thereby to measure said substance;
    wherein said physical parameter is density of field.

3. A method for detecting corporeal functional and metabolic data of a person by detecting in the person a substance which influences at least one of natural and artificial electric, electrochemical, and electromagnetic fields in the person, comprising:
    applying electrodes to the person;
    activating the electrodes alternatingly as sensors and as actuators;
    detecting signals resulting from said activating of the electrodes;
    said signals representing chances of a physical parameter of said natural and artificial electric, electrochemical, and electromagnetic fields;
    registering and storing the detected signals;
    inputting the stored signals into data processing equipment;
    processing the stored signals in the data processing equipment thereby to measure said substance;
    comprising detecting parallel reflected signals and classifying said reflected signals as being attributable to body temperature of the person.

4. A method for detecting corporeal functional and metabolic data of a person by detecting in the person a substance which influences at least one of natural and artificial electric, electrochemical, and electromagnetic fields in the person, comprising:
    applying electrodes to the person;
    activating the electrodes alternatingly as sensors and as actuators;
    detecting signals resulting from said activating of the electrodes;
    said signals representing changes of a physical parameter of said natural and artificial electric, electrochemical, and electromagnetic fields;
    registering and storing the detected signals;
    inputting the stored signals into data processing equipment;
    processing the stored signals in the data processing equipment thereby to measure said substance;
    comprising detecting parallel reflected signals and classifying said reflected signals as being attributable to skin resistance of the person.

5. A method for detecting corporeal functional and metabolic data of a person by detecting in the person a substance which influences at least one of natural and artificial electric, electrochemical, and electromagnetic fields in the person, comprising:
    applying electrodes to the person;
    activating the electrodes alternatingly as sensors and as actuators;
    detecting signals resulting from said activating of the electrodes;
    said signals representing changes of a physical parameter of said natural and artificial electric, electrochemical, and electromagnetic fields;
    registering and storing the detected signals;
    inputting the stored signals into data processing equipment;
    processing the stored signals in the data processing equipment thereby to measure said substance;
    comprising detecting parallel reflected signals and classifying said reflected signals as being attributable to gas exchange through the skin of the person per time unit.

6. An apparatus for detecting in a person a substance which influences at least one of natural and artificial electric, electrochemical and electromagnetic fields comprising:
    electrodes for application to the person and capable of alternatingly functioning as sensors and as actuators;
    an analog switch connected to the electrodes; connected to the switch an operational amplifier stage comprising an impedance converter amplifier;
    an analog-digital converter connected to the amplifier stage;

a digital signal processor connected to the amplifier stage and to the analog-digital converter; and connected to the processor a computer system stage for processing of thus normalized and digitalized signals;

means for wireless transmission of the field strength, field density, or parallel reflected signals which comprises an optical communication interface.

7. Method according to one of claims 1, 2 or 3–5, wherein said selecting, registering and storing is carried out continuously.

8. Method according to one of claims 1, 2 or 3–5, wherein said selecting, registering and storing is carried out discontinuously.

9. Method according to one of the claims 1, 2 or 3–5, wherein the electrodes are applied to predetermined skin areas of the person and affect said areas partially.

10. Method according to one of the claims 1, 2 or 3–5, wherein the electrodes are applied to predetermined skin areas of the person and affect said areas globally.

11. Method according to claim 10, wherein the detecting is in the form of points.

12. Method according to claim 10, wherein the detecting is in the form of a line.

13. Method according to claim 10, wherein the detecting is in the form of an area.

14. Method according to claim 2, wherein said physical parameter is a potential difference.

15. Method according to claim 2 wherein said physical parameter is amperage.

16. Method according to claim 2 wherein said physical parameter is voltage.

17. Method according to any one of claim 2, 14, 15 or 16, further comprising charting the detected signals.

18. Method according to claim 5, wherein the substance comprises lactate.

19. Method according to claim 5, wherein the substance comprises alcohol.

20. Method according to claim 5, wherein the substance comprises cholesterin.

21. Method according to claim 5, wherein the substance comprises stearin.

22. Method according to claim 5, wherein the substance comprises protein.

23. Method according to claim 5, wherein the substance comprises a drug.

24. Method according to claim 5, wherein the substance comprises blood lipids.

25. Method according to claim 5, wherein the substance comprises glucose.

26. Method according to claim 5, wherein the substance comprises blood sugar.

27. Apparatus according to claim 6, wherein individual components are arranged separately.

28. Apparatus according to claim 6, wherein the electrodes are arranged in groups.

29. Apparatus according to claim 28, wherein the groups comprise a matrix.

30. Apparatus according to claim 29, wherein at least part of the apparatus is implantable in the person.

31. Apparatus according to claim 30, wherein the amplifier stage is adapted to physical properties of the electrodes.

32. Apparatus according to claim 31, wherein the analog-digital converter together with the digital signal processor is scalable according to the number of primary contacts to be used.

33. Apparatus according to claim 32, wherein the computer system stage is scalable.

34. Apparatus according to claim 33, further comprising a generator connected to the electrodes through the switch for enabling each electrode to function alternatingly as a sensor or an actuator.

35. Apparatus according to claim 34, further comprising a display connected to the computer system stage.

36. Apparatus according to claim 35, further comprising a storage unit integrated with the computer system stage.

37. Apparatus according to claim 36, wherein the amplifier stage further comprises a filter connected to the preamplifier for elimination of interferences.

38. Apparatus according to claim 37, wherein the filter is multistage.

* * * * *

UNITED STATES PATENT AND TRADEMARK OFFICE
CERTIFICATE OF CORRECTION

PATENT NO. : 7,096,126 B2  Page 1 of 1
APPLICATION NO. : 10/474398
DATED : August 22, 2006
INVENTOR(S) : Ernst Geutebrueck It is certified that error appears in the above-identified patent and that said Letters Patent is hereby corrected as shown below:

Title Page;
Please correct the name and city address of the Assignee from:

(73) Assignee: Texmed Aktiengesellschaft, Brandenburg (DE)

to

(73) Assignee: Texmed GmbH, Potsdam (DE)

Signed and Sealed this

Twenty-ninth Day of January, 2008

JON W. DUDAS
*Director of the United States Patent and Trademark Office*